United States Patent [19]

Nakane et al.

[11] 4,456,615

[45] Jun. 26, 1984

[54] 7-OXABICYCLOHEPTANE SUBSTITUTED AMINO PROSTAGLANDIN ANALOGS AND THEIR USE IN INHIBITING PLATELET AGGREGATION AND BRONCHOCONSTRICTION

[75] Inventors: Masami Nakane, Plainsboro, N.J.; David L. Snitman, Boulder, Colo.; Joyce Reid, Dayton; Martin F. Haslanger, Lambertville, both of N.J.

[73] Assignee: E. R. Squibb & Sons, Inc., Princeton, N.J.

[21] Appl. No.: 436,741

[22] Filed: Oct. 25, 1982

[51] Int. Cl.³ .................. A61K 31/34; C07D 307/00
[52] U.S. Cl. ................................. 424/285; 549/463
[58] Field of Search .................... 549/463; 424/285

[56] References Cited

U.S. PATENT DOCUMENTS

| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 43292   6/1982  European Pat. Off. .
2039909 8/1980  United Kingdom .

Primary Examiner—Henry R. Jiles
Assistant Examiner—Bernard Dentz
Attorney, Agent, or Firm—Lawrence S. Levinson; Burton Rodney

[57] ABSTRACT

7-Oxabicycloheptane substituted amino prostaglandin analogs are provided having the structural formula

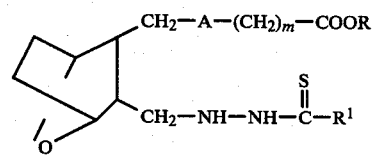

and including all stereoisomers thereof.

The compounds are cardiovascular agents useful, for example, in the treatment of thrombolytic disease.

13 Claims, No Drawings

7-OXABICYCLOHEPTANE SUBSTITUTED AMINO PROSTAGLANDIN ANALOGS AND THEIR USE IN INHIBITING PLATELET AGGREGATION AND BRONCHOCONSTRICTION

DESCRIPTION OF THE INVENTION

The present invention relates to 7-oxabicycloheptane substituted amino prostaglandin analogs which are cardiovascular agents useful, for example, in the treatment of thrombolytic disease. These compounds have the structural formula

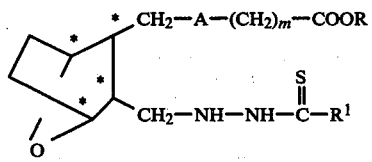

and including all stereoisomers thereof, wherein

A is $CH=CH$ or $(CH_2)_2$; m is 1 to 8; R is H or lower alkyl; and $R^1$ is lower alkyl, aryl, aralkyl, alkoxy, aralkoxy, alkylamino, arylamino or aralkylamino.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The term "$(CH_2)_m$" includes a straight or branched chain radical having from 1 to 8 carbons in the normal chain and may contain one or more lower alkyl substituents. Examples of $(CH_2)_m$ groups include $CH_2$, $CH_2CH_2$, $(CH_2)_3$, $(CH_2)_4$, $(CH_2)_5$, $(CH_2)_6$, $(CH_2)_7$,

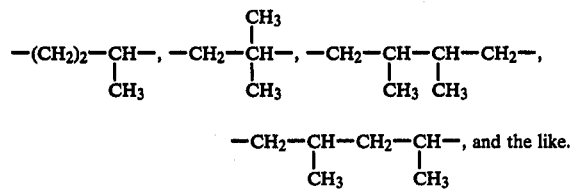

Preferred are those compounds of formula I wherein A is $(CH_2)_2$ or $CH=CH$, m is 2 to 4, R is H, and $R^1$ is phenylamino, benzylamino or alkylamino.

The various compounds of the invention may be prepared as outlined below.

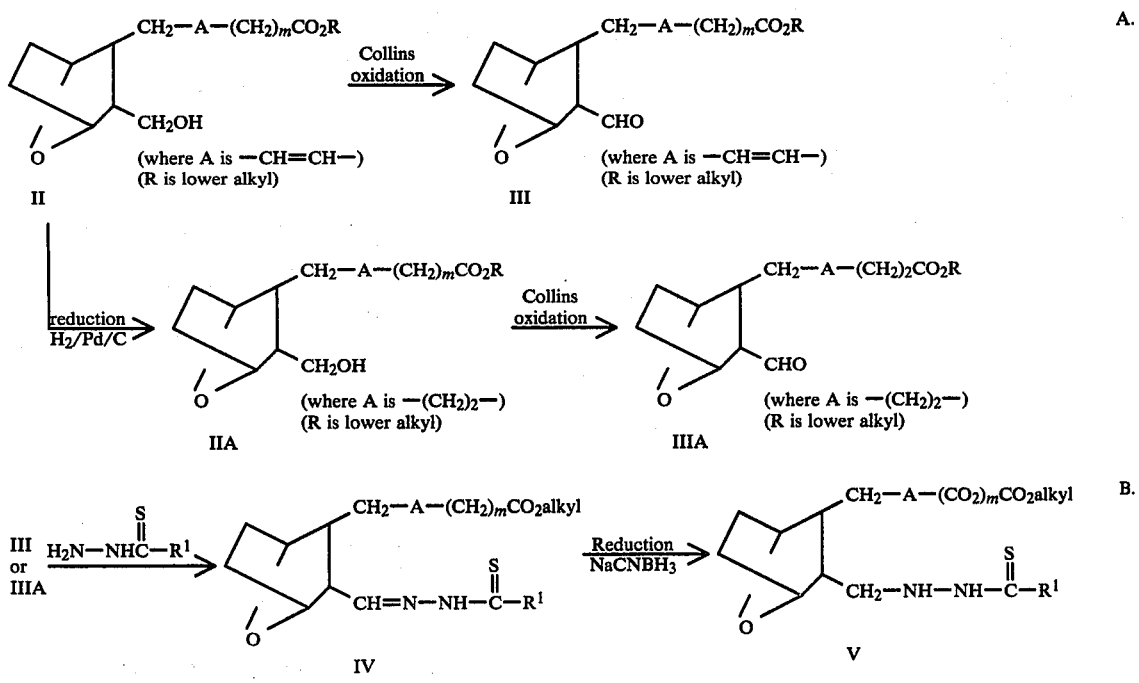

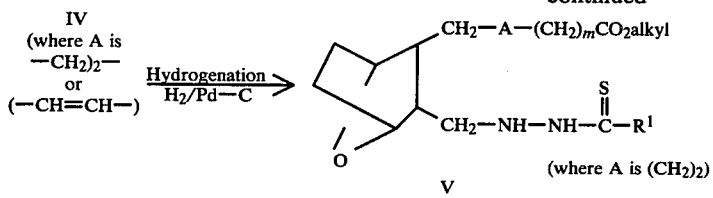

In the reaction sequence identified as "A", the starting lower alkyl ester containing the hydroxymethyl group, that is, compound II, (prepared as described in U.S. Pat. No. 4,143,054) is used to form the aldehyde III (where A is —CH=CH—) or IIIA (where A is —(CH$_2$)$_2$). Thus, to form aldehyde III where A is —CH=CH—, compound II is subjected to a Collins oxidation, for example, by reacting II with chromium trioxide and pyridine in methylene chloride. To form the aldehyde IIIA (where A is (CH$_2$)$_2$), compound II is reduced, for example with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$).

In the reaction sequence identified as "B", compounds of the invention wherein R is lower alkyl, that is

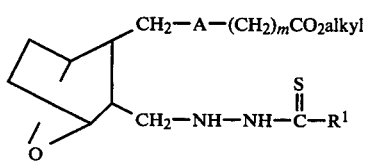

are prepared by reacting aldehyde III or IIIA with a hydrazine derivative

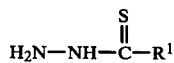

to form compound IV, employing a molar ratio of III or IIIA:A of within the range of from about 0.8:1 to about 1:1, in a protic solvent such as methanol or ethanol.

Compound IV is then reduced, such as by reacting IV with a reducing agent, such as NaBH$_3$CN or NaBH$_4$ in the presence of acetic acid to form compound V.

Compound V where A is —(CH$_2$)$_2$— may also be prepared by subjecting compound IV (where A is —(CH$_2$)$_2$— or —CH=CH—) to hydrogenation by reacting IV with hydrogen gas over a palladium on carbon catalyst.

The ester V can be converted to the free acid, that is, to

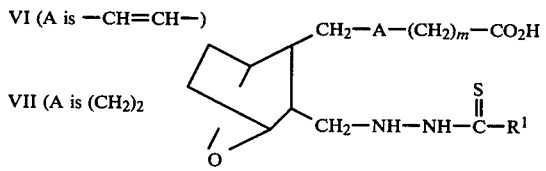

by treating the esters with a base, such as lithium hydroxide, followed by neutralization with an acid, such as dilute hydrochloric acid or oxalic acid.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

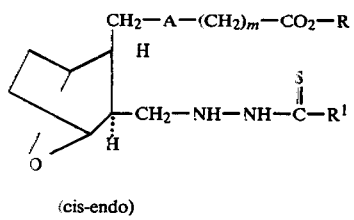

(cis-endo)

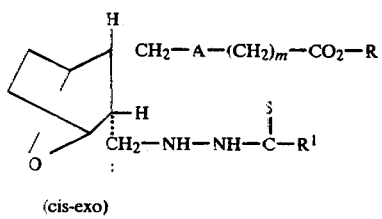

(cis-exo)

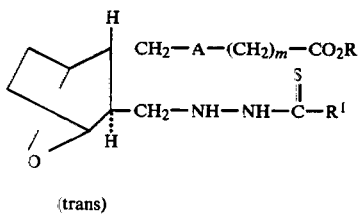

(trans)

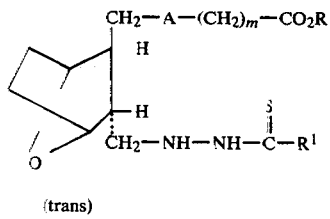

(trans)

The nucleus in each of the compounds of the invention is depicted as

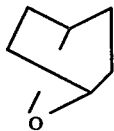

for matter of convenience; it will also be appreciated that the nucleus in the compounds of the invention may be depicted as

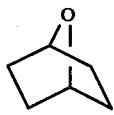

The compounds of this invention inhibit arachidonic acid-induced platelet aggregation and bronchoconstriction.

The compounds of this invention are cardiovascular agents useful as platelet aggregation inhibitors, e.g., for treatment of thrombolytic disease, such as coronary or cerebral thromboses. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of this invention.

EXAMPLE 1

[1β,2α(5Z),3α,4β]-7-[3-[[2-[(Phenylamino)thioxomethyl]hydrazino]methyl]-7-oxabicyclo[2.2.1]hept-2-yl]-5-heptenoic acid, methyl ester A. [1β,2α(5Z),3α,4β]-7-[3-Formyl-7-oxabicyclo[2.2.1]hept-2-yl]-5-heptenoic acid, methyl ester A solution of pyridine (14.3 ml, 177 mmol) in dichloromethane (500 ml) was treated portionwise wtih chromium trioxide (8.9 g, 8.9 mmoles) with vigorous stirring. After addition was complete, the mixture was stirred at room temperature for 30 minutes, then treated with celite (30 g), then [1β,2α(5Z),3α,4β]-7-[3-(hydroxymethyl)-7-oxabicyclo-[2.2.1]hept-2-yl]-5-heptenoic acid, methyl ester prepared as described in U.S. Pat. No. 4,143,054 (4 g, 14.96 mmoles) in dichloromethane (20 ml) was added dropwise over a 20 minute period. The reaction mixture was stirred at room temperature for 30 minutes then filtered through celite. The filtrate was washed with 5% sodium bicarbonate (2×250 ml), 10% hydrochloric acid (2×100 ml) and again with 5% sodium bicarbonate (2×250 ml). The dichloromethane solution was dried over magnesium sulfate, filtered and concentrated in vacuo. A brownish residue was dissolved in ether and passed through a pad of Baker silica gel, then eluted with more ether and the ether solution was taken to dryness in vacuo leaving 3.86 g of colorless oil.

B. [1β,2α(5Z),3α,4β]-7-[3-[[2-[(Phenylamino)thioxomethyl]hydrazino]methyl]-7-oxabicyclo[2.2.1]hept-2-yl]-5-heptenoic acid, methyl ester Aldehyde from part A (0.93 g, 3.5 mmol) and 4-phenylthiosemicarbazide (0.70 g, 4.2 mmol) were dissolved in ethanol (15 ml) and stirred at room temperature in an argon atmosphere for 3 hours. Sodium cyanoborohydride (0.33 g, 5.25 mmol) was then added followed by dropwise addition of glacial acetic acid (7.5 ml). The mixture was left stirring overnight at room temperature. After acidifying to pH 1 with 1N HCl stirring was continued for 1 hour. A small amount of water was added and after basification with solid NaHCO$_3$, the product was extracted into ether (3×100 ml). The combined ether extracts were washed with saturated NaHCO$_3$ solution (75 ml) and saturated NaCl solution (75 ml), dried (MgSO$_4$) and freed of solvent in vacuo to give a very viscous material (1.511 g). This was chromatographed on silica gel 60 (140 g) eluting with ether to give the title product (1.03 g, 68%) which became solid on standing. TLC: silica gel, Et$_2$O, UV and I$_2$; R$_f$=0.30.

EXAMPLE 2

[1β,2α(5Z),3α,4β]-7-[3-[[2-[(Phenylamino)thioxomethyl]-hydrazino]methyl]-7-oxabicyclo[2.2.1]hept-2-yl]-5-heptenoic acid The methyl ester from Example 1 (600 mg, 1.44 mmol) was dissolved in THF (60 ml) and water (10 ml) in an argon atmosphere and treated with 1N LiOH solution (14 ml). At the end of 2.5 hours the yellow reaction mixture was adjusted to pH 6 with 1N HCl solution (14 ml). The solution was poured into saturated NaCl solution (200 ml) and the products were extracted into ethyl acetate (3×100 ml). The combined ethyl acetate extracts were washed with saturated NaCl solution (4×75 ml), dried (MgSO$_4$) and freed of solvent in vacuo to give a yellow viscous material (584 mg). This was chromatographed on siliCAR CC-7 (40 g) eluting with 3% MeOH in CH$_2$Cl$_2$ to give pools rich in the two major products. The faster moving material (R$_f$=0.59 in 10% MeOH in CH$_2$Cl$_2$), 317 mg (54%) was identified by spectral data as the oxidation product, thiosemicarbazone. The other major product (200 mg, 34%; R$_f$=0.43) was identified as mainly the desired acid product. This material was rechromatographed on siliCAR CC-7 (22 g) eluting with 1 and 2% MeOH in CH$_2$Cl$_2$ to give clean title product (75 mg).

Anal Calc'd for C$_{21}$H$_{29}$O$_3$N$_3$S.0.3 H$_2$O: C, 61.68; H, 7.30; N, 10.28; S, 7.84 Found: C, 61.63; H, 7.07; N, 10.16; S, 7.66

EXAMPLE 3

[1β,2β,3α,4β]-7-[3-[[2-[(Phenylamino)thioxomethyl]-hydrazino]methyl]-7-oxabicyclo[2.2.1]hept-2-yl]-heptanoic acid A. [1β,2β,3β,4β]-7-[3-(Hydroxymethyl)-7-oxabicyclo[2.2.1]hept-2-yl]-heptanoic acid, methyl ester To 800 mg (3.0 mmole) of the [1β,2β(5Z),-3β,4β]-7-[3-(hydroxymethyl)-7-oxabicyclo[2.2.1]-hept-2-yl]-5- heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. [1β,2β,3β,4β]-7-[3-Formyl-7-oxabicyclo-[2.2.1]hept-2-yl]heptanoic acid, methyl ester To 1.21 g (5.6 mmole, 2.0 equiv.) of pyridinium-chlorochromate (PCC) and 20 ml of anhydrous $CH_2Cl_2$ was added, under an argon atmosphere, 730 mg (2.8 mmole) of the title A alcohol in 2 ml of $CH_2Cl_2$. The reaction was stirred for 2 hours at 25°, diluted with 100 ml of ether, filtered through a pad of florisil, and evaporated to furnish 670 mg (88%) of the title B compound as a white crystalline solid.

C. [1β,2β,3α,4β]-7-[3-Formyl-7-oxabicyclo-[2.2.1]hept-2-yl]heptanoic acid, methyl ester To 800.0 mg of the title B aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine, dried over anhydrous magnesium sulfate and concentrated to afford 765.0 mg (98%) of the title C aldehyde.

D. [1β,2β,3α,4β]-7-[3-[[2-[(Phenylamino)-thioxomethyl]hydrazino]methyl]-7-oxabicyclo[2.2.1]hept-2-yl]heptanoic acid Following the procedure of Examples 1 and 2, except substituting the Part C aldehyde for the Example 1A aldehyde, the title product is obtained.

EXAMPLE 4

[1β,2α(5Z),3β,4β]-7-[3-[[2-[(Phenylamino)thioxomethyl]hydrazino]methyl-7-oxabicyclo[2.2.1]hept-2-yl]-5-heptenoic acid A. [1β,2α(5Z),3β,4β]-7-[3-Formyl-7-oxabicyclo[2.2.1-]hept-2-yl]-5-heptenoic acid, methyl ester A solution of pyridine (14.6 ml) in dichloromethane (500 ml) was treated portionwise with chromium trioxide (9.06 g) with vigorous stirring. After addition was complete, the mixture was stirred at room temperature for 30 minutes then treated with celite (30 g) then [1β,2α(5Z),3β,4β]-7-[3-(hydroxymethyl)-7-oxabicyclo[2.2.1]hept-2-yl]-5-heptenoic acid, methyl ester prepared as described in U.S. Pat. No. 4,143,054 (4.05 g, 15.1 mmoles) in dichloromethane (25 ml). The reaction mixture was stirred at room temperature for 30 minutes then filtered through celite. The filtrate was washed with 5% sodium bicarbonate (2×300 ml), 10% hydrochloric acid (2×300 ml) and again with 5% sodium bicarbonate (1×300 ml). The dichloromethane solution was dried over magnesium sulfate and concentrated in vacuo. The residue was dissolved in ether, and filtered through a pad of Baker silica gel, washed with ether and the filtrate taken to dryness in vacuo leaving 3.79 g (92%) of pale yellow oil.

B. [1β,2α(5Z),3β,4β]-7-[3-[[2-[(Phenylamino)thioxomethyl]hydrazino]methyl]-7-oxabicyclo[2.2.1]hept-2-yl]-5-heptenoic acid Following the procedure of Examples 1 and 2, except substituting the part A aldehyde for the Example 1A aldehyde, the title product is obtained.

EXAMPLE 5

[1β,2β,3α,4β]-7-[3-[[2-[(Phenyl)thioxomethyl]-hydrazino]methyl]-7-oxabicyclo[2.2.1]hept-2-yl]-heptanoic acid Following the procedure of Example 3 except substituting phenylthiohydrazide for 4-phenylthiosemicarbazide, the title product is obtained.

EXAMPLE 6

[1β,2α(5Z),3β,4β]-7-[3-[[2-[(Phenyl)thioxomethyl]-hydrazino]methyl]-7-oxabicyclo[2.2.1]hept-2-yl]-5-heptenoic acid Following the procedure of Example 4 except substituting phenylthiohydrazide for 4-phenylthiosemicarbazide, the title product is obtained.

EXAMPLE 7

[1β,2β,3α,4β]-7-[3-[[2-[(Benzyl)thioxomethyl]-hydrazino]methyl]-7-oxabicyclo[2.2.1]hept-2-yl]-heptanoic acid Following the procedure of Example 3 except substituting benzylthiohydrazide for 4-phenylthiosemicarbazide, the title compound is obtained.

EXAMPLE 8

[1β,2α(5Z),3β,4β]-7-[3-[[2-[(Benzyl)thioxomethyl]-hydrazino]methyl]-7-oxabicyclo[2.2.1]hept-2-yl]-5-heptenoic acid Following the procedure of Example 4 except substituting benzylthiohydrazide for 4-phenylthiosemicarbazide, the title compound is obtained.

EXAMPLE 9

[1β,2β,3α,4β]-7-[3-[[2-[(Benzyloxy)thioxomethyl]-hydrazino]methyl]-7-oxabicyclo[2.2.1]hept-2-yl]-heptanoic acid Following the procedure of Example 3 except substituting benzyloxythiohydrazide for 4-phenylthiosemicarbazide, the title product is obtained.

EXAMPLE 10

[1β,2α(5Z),3β,4β]-7-[3-[[2-[(Benzyloxy)thioxomethyl]-hydrazino]methyl]-7-oxabicyclo[2.2.1]hept-2-yl]-5-heptenoic acid Following the procedure of Example 4 except substituting benzyloxythiohydrazide for 4-phenylthiosemicarbazide, the title compound is obtained.

EXAMPLE 11

[1β,2β,3α,4β]-7-[3-[[2-[(Benzylamino)thioxomethyl]-hydrazino]methyl-7-oxabicyclo[2.2.1]hept-2-yl]-heptanoic acid Following the procedure of Example 3 except substituting 4-benzylthiosemicarbazide for 4-phenylthiosemicarbazide, the title product is obtained.

EXAMPLE 12

[1β,2α(5Z),3β,4β]-7-[3-[[2-[(Benzylamino)thioxomethyl]-hydrazino]methyl]-7-oxabicyclo[2.2.1]hept-2-yl]-5-heptenoic acid Following the procedure of Example 4 except substituting 4-benzylthiosemicarbazide for 4-phenylthiosemicarbazide, the title compound is obtained.

EXAMPLE 13

[1β,2β,3α,4β]-7-[3-[[2-[(n-Butylamino)thioxomethyl]-hydrazino]methyl]-7-oxabicyclo[2.2.1]hept-2-yl]-heptanoic acid Following the procedure of Example 3 except substituting 4-n-butylthiosemicarbazide for 4-phenylthiosemicarbazide, the title compound is obtained.

EXAMPLE 14

[1β,2α(5Z),3β,4β]-7-[3-[[2-[(n-Butylamino)thioxomethyl]hydrazino]methyl]-7-oxabicyclo[2.2.1]hept-2-yl]-5-heptenoic acid Following the procedure of Example 4 except substituting 4-n-butylthiosemicarbazide for 4-phenylthiosemicarbazide, the title compound is obtained.

EXAMPLE 15

[1β,2β,3α,4β]-7-[3-[[2-[(Propylamino)thioxomethyl]-hydrazino]methyl-7-oxabicyclo[2.2.1]hept-2-yl]-heptanoic acid Following the procedure of Example 3 except substituting 4-propylthiosemicarbazide for 4-phenylthiosemicarbazide, the title product is obtained.

EXAMPLE 16

[1β,2α(5Z),3β,4β]-7-[3-[[2-[Propylamino)thioxomethyl]-methyl]-7-oxabicyclo[2.2.1]hept-2-yl]-5-heptenoic acid Following the procedure of Example 4 except substituting 4-propylthiosemicarbazide for 4-phenylthiosemicarbazide, the title product is obtained.

What is claimed is:

1. A compound having the structural formula

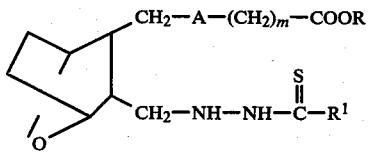

and including all stereoisomers thereof;
wherein A is CH=C or (CH$_2$)$_2$;
m is 1 to 8; R is H or lower alkyl; and R$^1$ is lower alkyl, lower alkoxy, aryl, aralkyl, aralkoxy, alkylamino, arylamino or aralkylamino, wherein the term alkyl or lower alkyl by itself or as part of another group contains 1 to 12 carbons, the term aryl by itself or as part of another group refers to a monocyclic or bicyclic aromatic group which contains 6 to 10 carbon atoms in the ring and which ring may be unsubstituted or substituted with a halogen, lower alkyl or lower alkoxy group.

2. The compound as defined in claim 1 having the formula

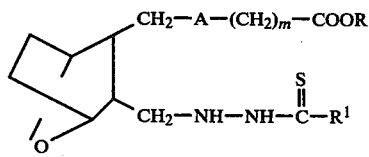

wherein R$^1$ is phenylamino including all stereoisomers thereof.

3. The compound as defined in claim 1 having the formula

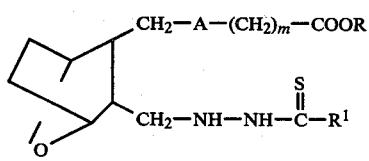

wherein R$^1$ is lower alkyl or aralkyl including all stereoisomers thereof.

4. The compound as defined in claim 2 wherein A is (CH$_2$)$_2$.

5. The compound as defined in claim 2 wherein A is CH=CH.

6. The compound as defined in claim 4 wherein m is 3.

7. The compound as defined in claim 1 wherein R is H.

8. The compound as defined in claim 1 having the name [1β,2α(5Z),3α,4β]-7-[3-[[(phenylamino)-thioxomethyl]hydrazino]methyl]-7-oxabicyclo[2.2.1]hept-2-yl]-5-heptenoic acid or the methyl ester thereof including all stereoisomers thereof.

9. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

10. The method as defined in claim 9 wherein said compound is administered in an amount within the range of from about 1 to about 100 mg/kg.

11. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

12. A method of inhibiting platelet aggregation which comprises administering to a mammalian host an effective amount of a compound as defined in claim 1 or a pharmaceutically acceptable salt thereof.

13. A method of inhibiting bronchoconstriction associated with asthma, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,456,615
DATED : June 26, 1984
INVENTOR(S) : Masami Nakane et al.

It is certified that error appears in the above-identified patent and that said Letters Patent is hereby corrected as shown below:

Column 4, the structures on lines 30 - 65 should read as follows:

Ia
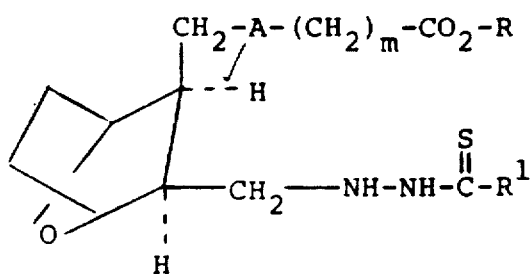
(cis-endo)

Ib
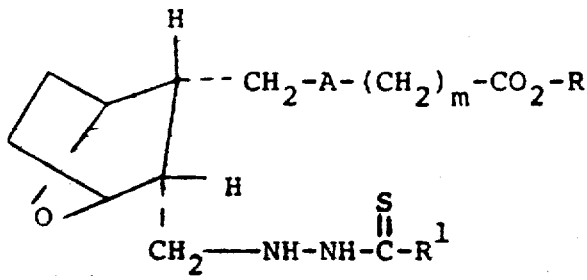
(cis-exo)

UNITED STATES PATENT AND TRADEMARK OFFICE
CERTIFICATE OF CORRECTION

PATENT NO. : 4,456,615

DATED : June 26, 1984

INVENTOR(S) : Masami Nakane et al.

It is certified that error appears in the above-identified patent and that said Letters Patent is hereby corrected as shown below:

Ic 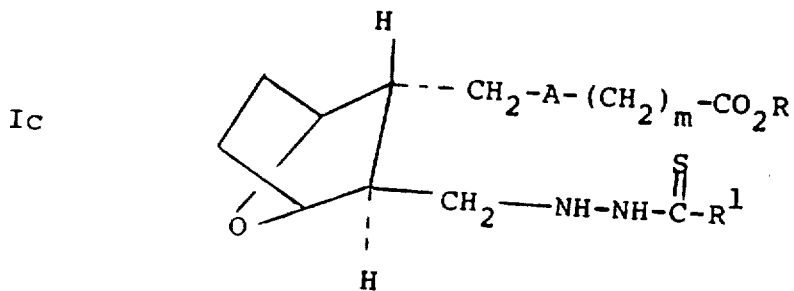

(trans)

UNITED STATES PATENT AND TRADEMARK OFFICE
CERTIFICATE OF CORRECTION

PATENT NO. : 4,456,615

DATED : June 26, 1984

INVENTOR(S) : Masami Nakane et al.

It is certified that error appears in the above-identified patent and that said Letters Patent is hereby corrected as shown below:

Id

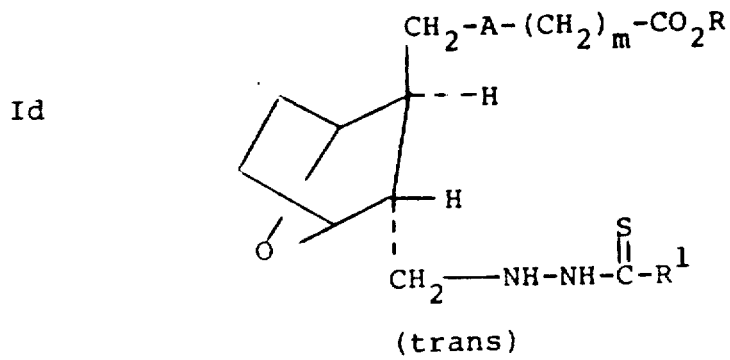

(trans)

Signed and Sealed this

Twelfth Day of March 1985

[SEAL]

Attest:

DONALD J. QUIGG

Attesting Officer     Acting Commissioner of Patents and Trademarks